United States Patent [19]
Galliano, II

[11] Patent Number: 5,709,467
[45] Date of Patent: Jan. 20, 1998

[54] DEVICE AND APPARATUS FOR MIXING ALGINATE

[76] Inventor: Carol J. Galliano, II, 17845 E. Augusta Dr., Baton Rouge, La. 70810

[21] Appl. No.: 665,431

[22] Filed: Jun. 18, 1996

[51] Int. Cl.$^6$ .................. B65D 33/16; B65D 33/36; B28C 3/00

[52] U.S. Cl. .................. 366/130; 366/3; 366/50; 366/189; 206/219; 383/63

[58] Field of Search .................. 366/1, 2, 3, 10, 366/129, 130, 189, 348, 349, 602, 53, 40; 206/219, 220, 221; 433/80, 89; 383/63, 67, 97, 96, 95; 24/118

[56] References Cited

U.S. PATENT DOCUMENTS

| | | | |
|---|---|---|---|
| 716,677 | 12/1902 | Cruttenden | 433/89 |
| 749,846 | 1/1904 | Cruttenden | 433/89 |
| 1,341,736 | 6/1920 | Cruttenden | 433/89 |
| 3,018,880 | 1/1962 | Brugmann | 206/219 |
| 3,851,688 | 12/1974 | De Winter | 383/96 |
| 3,860,219 | 1/1975 | Nickerson, Jr. | 366/3 |
| 4,470,703 | 9/1984 | Nickerson, Jr. | 366/3 |
| 4,557,377 | 12/1985 | Maloney | 206/219 |
| 4,614,267 | 9/1986 | Larkin | 383/96 |
| 4,818,544 | 4/1989 | Seward | 383/67 |
| 4,903,718 | 2/1990 | Sullivan | 383/63 |
| 5,240,112 | 8/1993 | Newburger | 383/63 |
| 5,261,532 | 11/1993 | Fauci | 383/63 |

FOREIGN PATENT DOCUMENTS

| | | | |
|---|---|---|---|
| 1167881 | 12/1958 | France | 383/96 |
| 667522 | 9/1964 | Italy | 383/96 |

*Primary Examiner*—Tony G. Soohoo
*Attorney, Agent, or Firm*—Roy, Kiesel & Tucker

[57] ABSTRACT

A device for and a method of mixing and dispensing alginate is disclosed. The invention entails a pouch having a sealable aperture through which alginate and water may be added. The pouch also has an sealable spout. The function of these two openings may be performed by a single opening. When the alginate and water are in the pouch, a dentist will mix the two together by manipulating the pouch with his hands. When the contents of the pouch are thoroughly mixed, the spout may be opened and the pouch evacuated. When the pouch is empty, it may be discarded.

6 Claims, 2 Drawing Sheets

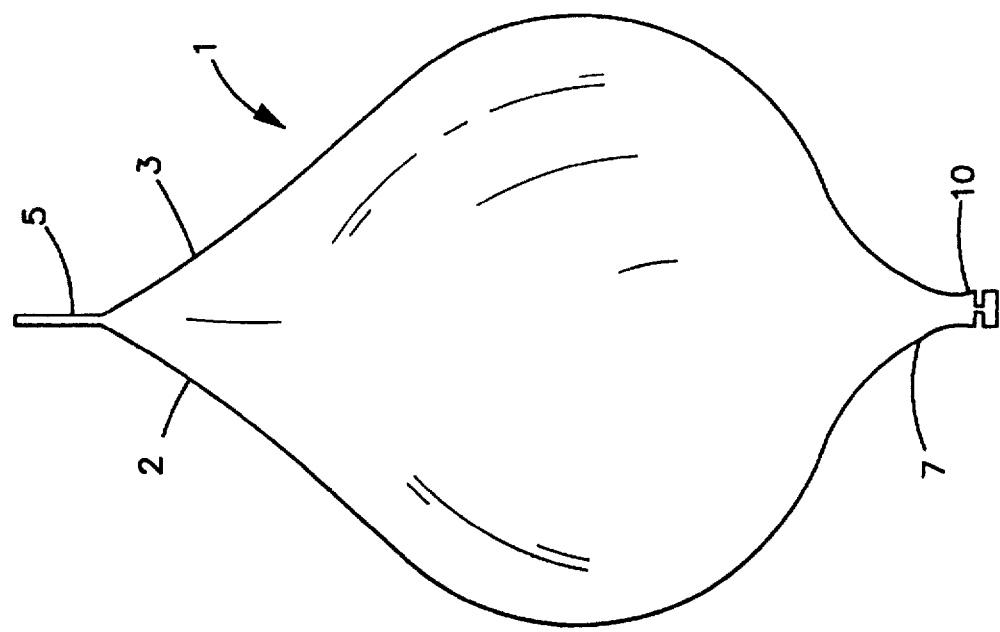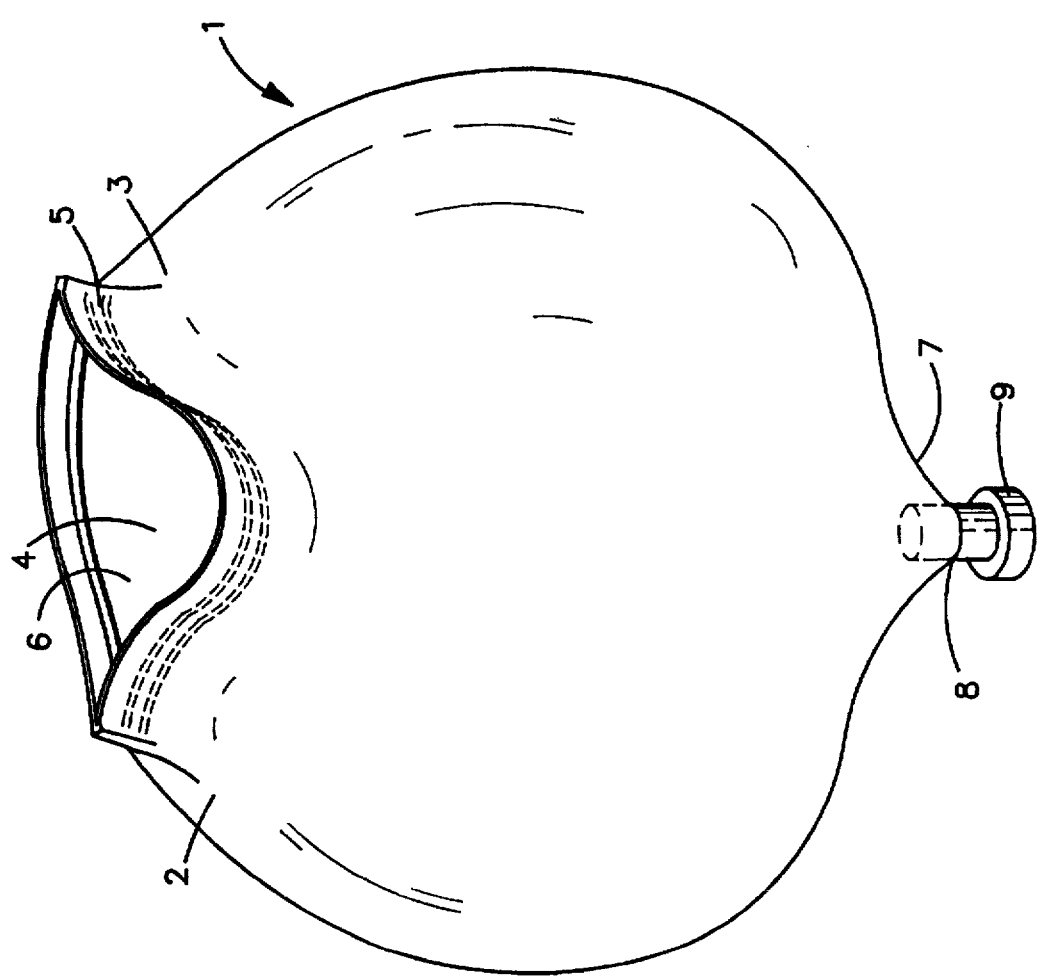

DEVICE AND APPARATUS FOR MIXING ALGINATE

BACKGROUND OF THE INVENTION

1. Field of the Invention

The invention relates generally to a device for and a method of mixing and dispensing alginate.

2. Prior Art

The prior art consists largely of the use of mixing bowls and spatulas in the preparation of pastes used for dental impressions.

The term alginate is used herein to refer to an irreversible alginate-based hydrocolloid. Many commercially available sources of alginate are comprised of ≈12–15% sodium alginate (reactant), ≈8–12% calcium sulfate dihydrate (reactant), ≈2% sodium phosphate or sodium carbonate (retarder), and ≈70% reinforcing filler such as diatomaceous earth. Alginate is available commercially under the brand names "Algident," "Coe-Alginate," "Hydro-Jel,"0 "Jeltrate" and "Supergel" among others. Dentists use alginate to prepare castings of their patients' teeth. Initially, the alginate is in a dry powder. The dentist will place a certain amount of the alginate into a bowl and add water. The amount of alginate powder and water required will vary depending upon the brand used. This information is generally provided by the alginate manufacturer.

The alginate/water mixture must have a pasty gel-like flowable consistency. It cannot be too soupy, nor too dry, and powdery "pockets" in the mix are unsatisfactory. Thus, the water must be added in exact proportions and then mixed thoroughly to ensure that the water is evenly distributed. This generally entails mixing the alginate in a bowl either with a spatula or by machine. The spatula method is messy while the machine method requires the purchase of a machine. Both methods require clean up after the mixing is finished. In addition, the spatula method also requires a certain level of skill. The alginate and water must be mixed vigorously to ensure thorough distribution of the water to all the powder. However, the mixing must be gentle until the mixture becomes substantially pasty in order to avoid loss of the powder.

After the mixture is formed, the dentist will place it in a mouth sized preformed impression tray that will then be placed in the patient's mouth to form an imprint of his or her teeth. When the alginate hardens, it can be used to form a casting of the patients'teeth by pouring an alpha modified gypsum or plaster-of-Paris or another similar substance into the imprint. The mixing process and the transfer of the mixture from the bowl to the tray often result in loss of some of the mixture.

OBJECTS OF THE INVENTION

It is an object of the invention to more cleanly prepare an alginate/water mixture.

It is another object of the invention to provide a means of thoroughly and economically mixing alginate with water.

It is another object of the invention to make the preparation of the alginate/water mixture more efficient.

It is still another object of the invention to reduce the loss of alginate and of the alginate/water mixture.

It is a still further object of the invention to ensure the correct ratio of alginate and water.

It is a still further object of the invention to eliminate the time and effort necessary for the cleanup of the bowl and spatula after use.

It is yet another object of the invention to simplify the mixing process so to eliminate the training and practice required to perform prior art alginate mixing methods.

SUMMARY OF THE INVENTION

A pouch for and a method of mixing and dispensing alginate is disclosed. The pouch comprises an envelope having wall sections that form a sealable cavity. At least one wall section contains a sealable opening through which alginate and water may be added. The pouch may also have a sealable spout through which the contents of the pouch may be evacuated. The function of these two openings may be performed by a single opening. Preferably, the pouch should be made of clear plastic or at least contain clear windows.

The dentist will place the alginate in the pouch and add the appropriate amount of water. Alternatively, the pouch may be sold with a premeasured quantity of alginate already in it, so that all the dentist has to do is add water. Although the desired ratio of alginate to water may change depending on the commercial source, a typical ratio is 7 gm powder:19 cc water at 23° C.

After the water and alginate have been placed in the pouch, it should be closed. All openings in the pouch should be sealable. The dentist may then mix the powder and water by hand without getting any of the mixture on his hands. The best manner of mixing known to the inventor entails the dentist rubbing the pouch between his palms vigorously in a circular fashion for ≈30 –60 sec. until a flowable doughy consistency has been obtained. He may visually determine when the mixture is properly mixed by looking for and eliminating dry spots. When the mixture is thoroughly mixed, the dentist will open the spout and squeeze the pouch steadily to control the outflow. The dentist may thereby obtain an even fill of the impression tray. In a preferred embodiment, the pouch may be fully evacuated by squeezing it from the top and working down toward the spout. When finished, the pouch may be thrown away, eliminating the need for cleanup.

BRIEF DESCRIPTION OF THE DRAWING

FIG. 1 is a depiction of a preferred embodiment of an alginate mixing pouch.

FIG. 2 is a side view of the alginate mixing pouch depicted in FIG. 1.

DETAILED DESCRIPTION OF PREFERRED EMBODIMENTS OF THE INVENTION

Figure 3:
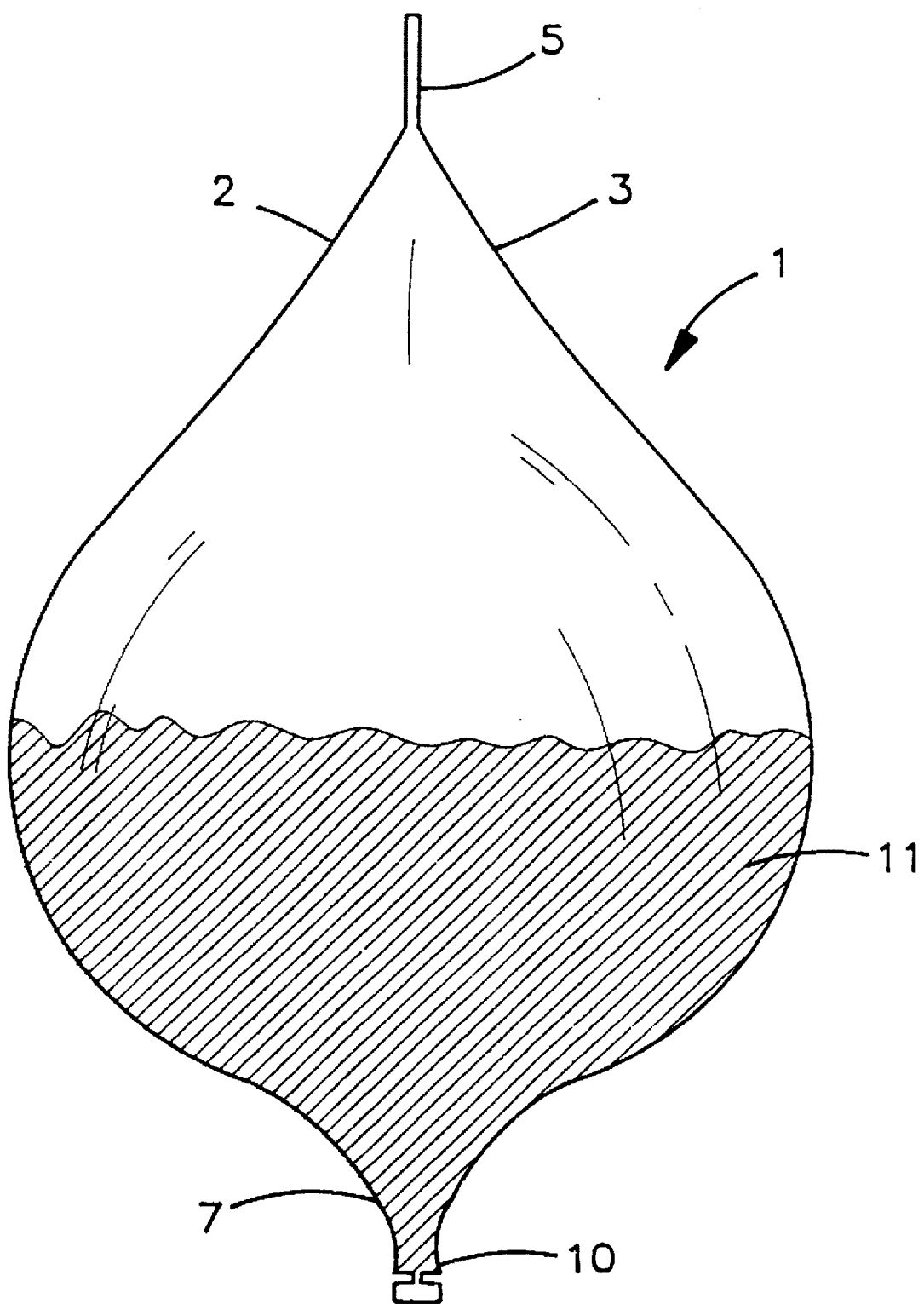
FIG. 3 is a side view of the preferred embodiment shown in FIG. 2 after the alginate has been added to the mixing pouch.

As shown in FIG. 1, a pouch 1 for mixing alginate 11 and water or other substances is disclosed. Pouch 1 comprises an envelope 2 having one or more wall sections 3 that form a sealable cavity 4. Wall sections 3 are preferably made of a clear flexible watertight material such as plastic. Wall sections 3 should be strong enough to withstand mixing alginate 11 without breaking. Wall sections 3 should be sufficiently flexible to allow the dentist to mix the alginate 11 and water contained within cavity 4 by manipulating wall sections 3 with his hands. It has been found that plastic wall sections 3 having a thickness between about 1.15 mils and about 2.7 mils are sufficient. However, the thinner pouch 1 is, the better the dentist will be able to feel the consistency of the mixture. Depending upon the strength and type of plastic or other material used, it may be possible to make wall sections 3 thinner than about 1.15 mils.

In a preferred embodiment, pouch 1 will be shaped like a pear. This shape is less conducive to the formation of pockets of dry alginate 11 because it has no corners. However, any shape of pouch 1, such as a square shape or an elongated tubular shape, will work. Pouch 1 should allow the dentist to see its contents. Therefore, it is preferable that wall sections 3 be made of clear plastic or another transparent substance or that pouch 1 be provided with clear windows.

Pouch 1 should contain an opening means 5 for providing passage into pouch 1. Opening means 5 may comprise an aperture 6 in pouch 1. Aperture 6 is preferably sealable with an adhesive strip, a zipper, a Ziploc® type locking strip or other similar device. However, aperture 6 may be closed with a twist-tie, or a cable-tie or even by knotting pouch 1. The dentist will use opening means 5 to add alginate 11 and water to pouch 1.

Pouch 1 should also contain a dispensing means 7 for dispensing the contents of cavity 4. Dispensing means 7 may comprise a spout 8 or other similar opening. Dispensing means 7 should be sealable, preferably with a stopper 9. Alternatively, dispensing means 7 may be formed by the dentist after mixing is complete by cutting a hole in pouch 1. As shown in FIG. 2, dispensing means 7 may comprise a closed flat but frangible spout 10 which the dentist may twist off by hand or snip with a pair of scissors. Also, the functions of dispensing means 7 and opening means 5 may be performed by a single opening.

A preferred embodiment of the invention comprises a kit for preparing alginate pastes. The kit comprises a premeasured quantity of alginate 11 powder and pouch 1. Aperture 6 of pouch 1 will be sized to permit introduction of the alginate 11 powder into cavity 4.

In operation, the dentist will add alginate 11 to pouch 1 through opening means 5. Alternatively, the alginate 11 may be placed in pouch 1 by the manufacturer. When the manufacturer adds the alginate 11, a measurement step may be eliminated for the dentist, thereby reducing the likelihood of error in mixing. After the alginate 11 is in pouch 1, the dentist will add water through opening means 5. Alternatively, the dentist may add the water first. The dentist will then close opening means 5 and begin to mix the contents of pouch 1 by rubbing pouch 1 between his palms. As the dentist is mixing, clumps will often form in the mix. These clumps contain dry or partially dry powder and resist the introduction of water to that powder. By mixing in pouch 1, the dentist may easily break those clumps by hand and allow water to reach the powder they contain.

The dentist will continue to mix until the water and alginate 11 are thoroughly mixed and no dry sections or clumps remain. This should take about 30 to 60 seconds. When the mixing is complete, the dentist will open dispensing means 7. Preferably, he will form pouch 1 into a funnel shape with his hands. He will then evacuate the contents of pouch 1 via dispensing means 7 into the tray. When pouch 1 is empty, it may be thrown away.

The tray will be placed into the patient's mouth to create an imprint of the patient's teeth. When the imprint hardens, alpha modified gypsum or plaster-of-Paris or another similar substance may be poured into the imprint to form a casting of the patient's teeth. Other uses and embodiments of the invention will occur to those skilled in the art, and are intended to be included within the scope and spirit of the following claims.

I claim:

1. An alginate paste preparation kit comprising:

a premeasured quantity of alginate powder; and a mixing pouch comprising an envelope having flexible wall sections forming a sealable cavity, at least one wall section having a sealable aperture sized to permit the introduction of said alginate powder and liquids into said cavity, at least one wall section containing a sealable spout sized to permit the evacuation of the contents of said cavity.

2. An alginate paste preparation kit according to claim 1 wherein said wall sections are sufficiently flexible to allow powders and liquids within said cavity to be mixed by manipulating said wall sections.

3. An alginate paste preparation kit according to claim 1 wherein said wall sections are shaped to give said pouch a pear shape.

4. An alginate paste preparation kit according to claim 1 wherein said wall sections are constructed from transparent plastic.

5. An alginate paste preparation kit according to claim 1 wherein said wall sections are constructed from transparent plastic having a thickness of at least about 1.15 mils.

6. An alginate paste preparation kit according to claim 1 wherein said wall sections are constructed from transparent plastic having a thickness of about 2.7 mils.

* * * * *